United States Patent [19]
Nagano et al.

[11] Patent Number: 4,578,465
[45] Date of Patent: Mar. 25, 1986

[54] PHENYLPIPERAZINE DERIVATIVES

[75] Inventors: Hiroyuki Nagano; Mitiro Takagi; Noboru Kubodera, all of Saitama; Isao Matsunaga; Hiroyuki Nabata, both of Tokyo; Yasuhiro Ohba, Kanagawa; Kazushige Sakai, Tokyo; Shun-ichi Hata, Kanagawa; Yasumi Uchida, Chiba, all of Japan

[73] Assignee: Chugai Seiyaku Kabushiki Kaisha, Tokyo, Japan

[21] Appl. No.: 604,415

[22] Filed: Apr. 30, 1984

Related U.S. Application Data

[63] Continuation-in-part of Ser. No. 473,317, Mar. 8, 1983, abandoned.

[30] Foreign Application Priority Data

Mar. 17, 1982 [JP] Japan .................. 57-40904

[51] Int. Cl.⁴ ................ C07D 403/06; A61K 31/505
[52] U.S. Cl. ................................. 544/285
[58] Field of Search ........................ 544/285

[56] References Cited

U.S. PATENT DOCUMENTS

| | | | |
|---|---|---|---|
| 3,274,194 | 9/1966 | Hayao | 544/284 |
| 3,322,766 | 5/1967 | Schipper | 544/287 |
| 3,726,979 | 4/1973 | Hong | 424/250 |
| 3,819,630 | 6/1974 | Parcell | 424/251 |
| 3,879,393 | 4/1975 | Havera | 424/251 |

FOREIGN PATENT DOCUMENTS

| | | | |
|---|---|---|---|
| 6124 | 11/1967 | Australia . | |
| 269143 | 3/1969 | Austria | 544/285 |
| 0040793 | 12/1981 | European Pat. Off. . | |
| 1934037 | 1/1971 | Fed. Rep. of Germany | 544/285 |
| 1227936 | 4/1971 | United Kingdom . | |

Primary Examiner—Glennon H. Hollrah
Assistant Examiner—James H. Turnipseed
Attorney, Agent, or Firm—Browdy and Neimark

[57] ABSTRACT

Phenylpiperazine derivatives of the formula:

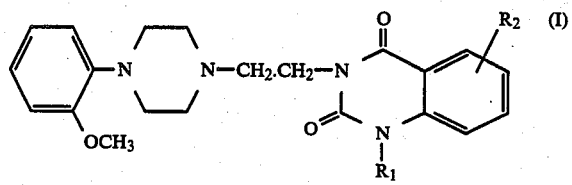

wherein $R_1$ is a hydrogen atom or a straight- or branched-chain saturated or unsaturated alkyl group having 1 to 8 carbon atoms which may be substituted at any position by a hydroxyl group, a carboxyl group, a lower alkoxycarbonyl group or an oxo group; and $R_2$ is a hydrogen atom, a halogen atom, a lower alkyl group or a sulfamoyl group, and a process for producing the same are disclosed. The derivatives of the formula have alpha blocking and serotonin antagonizing activities and are useful as a drug.

5 Claims, No Drawings

PHENYLPIPERAZINE DERIVATIVES

This application is a continuation-in-part of copending parent application Ser. No. 473,317, filed Mar. 8, 1983, now abandoned without prejudice in favor of the present application.

The present invention relates to phenylpiperazine derivatives of formula (I):

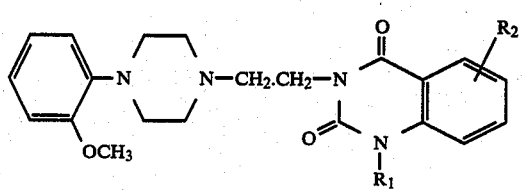

wherein $R_1$ is a hydrogen atom or a straight- or branched-chain saturated or unsaturated alkyl group having 1 to 8 carbon atoms which may be substituted at any position by a hydroxyl group, a carboxyl group, a lower alkoxycarbonyl group (wherein the alkyl group moiety may preferably have 1 to 3 carbon atoms) or an oxo group; and $R_2$ is a hydrogen atom, a halogen atom, a lower alkyl (preferably having 1 to 3 carbon atoms) or a sulfamoyl group.

The compounds of formula (I) have alpha blocking and serotonin antagonizing activities, so they can be used as long lasting potent antihypertensives and vasodilators for peripheral vessels.

The compounds of formula (I) are novel and can be prepared by the following illustrative method:

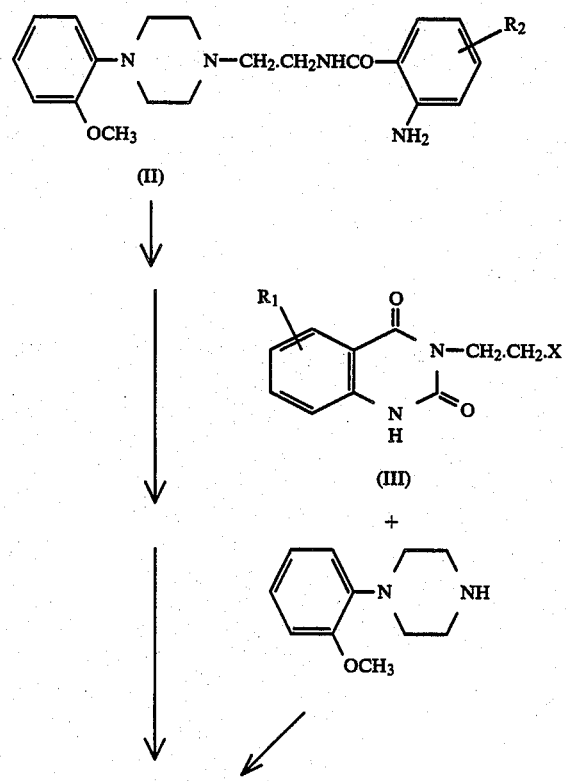

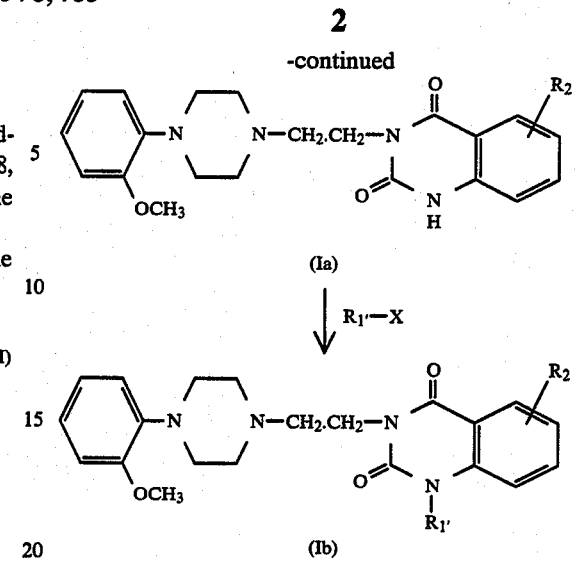

wherein $R_2$ is the same as defined above; and $R_{1'}$ is a straight- or branched-chain saturated or unsaturated alkyl group having 1 to 8 carbon atoms which may be substituted at any position by a hydroxyl group, a carboxyl group, a lower alkoxycarbonyl group (wherein the alkyl group moiety is preferably $C_1$–$C_3$) or an oxo group; X is a halogen atom.

According to this reaction scheme, one of the compounds of the present invention which is represented by formula (Ia) can be prepared by one of the following methods: (a) 1-(2-methoxyphenyl)piperazine is treated by the method described in Japanese Patent Publication No. 19065/70 to prepare a compound of formula (II), which is reacted with trichloromethyl chloroformate in an inert organic solvent in the presence of a base such as sodium hydrogencarbonate or triethylamine, or heated in dimethylformamide together with urea, or heated in an inert organic solvent together with phosgene; or (b) 3-(2-halogenoethyl)-2,4(1H,3H)-quinazolinedione derivative of formula (III) is heated in dimethylformamide in the presence of potassium carbonate and sodium iodide together with 1-(2-methoxyphenyl)piperazine. Subsequently, the compound (Ia) is reacted with an alkyl halide to form a compound of formula (Ib). The reaction is generally effected by heating the reactants in an organic solvent such as ethanol or dimethylformamide in the presence of sodium hydride and sodium iodide. If the alkyl group represented by $R_{1'}$ in formula (Ib) has a hydroxyl group, the conversion from (Ia) to (Ib) is preferably effected after protecting this hydroxyl group into another form such as an oxo group or an acyloxy group, say, an acetoxy group. The oxo group in the resulting compound can be readily converted to a hydroxyl group by subjecting it to reduction with, say, a metal hydride such as sodium borohydride, and the acyloxy group such as an acetoxy group can be easily converted to a hydroxyl group by subjecting it to ordinary hydrolysis, say, with an alcoholic aqueous solution of sodium hydroxide or potassium hydroxide. If the alkyl group represented by $R_{1'}$ contains a carboxyl group, it may also be protected into, say, an ester form, before conversion to compound (Ib), and the resulting compound is hydrolyzed to reconvert the ester to a carboxyl group.

In the reactions described above, the end compound can be readily isolated from the reaction mixture by any conventional technique such as the addition of water to the reaction mixture followed either by filtration and recrystallization of the resulting crystal or by extraction with an organic solvent such as methylene chloride or chloroform, the distilling off of the solvent, and recrystallization or column chromatography.

The compounds (I) of the present invention may form salts with organic or inorganic acids. Pharmaceutically acceptable salts are preferred, and inorganic examples are hydrochloric acid, sulfuric acid, nitric acid and phosphoric acid, and organic examples include fumaric acid, maleic acid, tartaric acid and succinic acid. Salts of the compounds (I) with these acids can be easily formed by any of the conventional methods.

The hypotensive effect and acute toxicity of a compound (I) of the present invention were examined in the following experiments.

EXPERIMENT (a) Hypotensive effect: A bulk powder or compound No. 3-b (as prepared in Example 3 to be described later in this specification) was dissolved in distilled water. Beagles anesthetized by intravenous injection of pentobarbital sodium and subjected to thoracotomy under artificial ventilation were treated intravenously with 1 to 30 μg/kg of compound No. 3-b. The mean systemic blood pressure was reduced by 20 to 40 mmHg over a period of about one hour. The heart rate was decreased slightly. When compound No. 3-b (1 mg/kg) was administered to the duodenums of beagles, the systemic blood pressure and the heart rate were reduced by about 30 mmHg and by 10%, respectively. The effects lasted for at least 7 hours. The systemic blood pressure was measured by means of a pressure transducer connected to a catheter inserted into the right femoral artery. The heart rate was measured with a cardiometer.

(b) Acute toxicity: Four SD strain rats were given orally compound No. 3-b. All animals survived by a dose level of 2 g/kg. It was therefore concluded that the $LD_{50}$ of compound No. 3-b was more than 2 g/kg.

The present invention is described by the following examples which are given here for illustrative purposes only and are by no means intended to limit the scope of the invention.

EXAMPLE 1

(a) A mixture of 1-(2-methoxyphenyl)-4-[2-(2-aminobenzoyl)-aminoethyl]piperazine (3.54 g) and triethylamine (2.2 g) was dissolved in methylene chloride (50 ml), and the resulting solution was added dropwise to a solution of trichloromethyl chloroformate (0.989 g) in methylene chloride (20 ml) under stirring at between −5° and 5° C. Then, the mixture was gradually heated to room temperature at which it was held for 1 to 2 hours to effect reaction. After completion of the reaction, saturated aqueous sodium hydrogencarbonate was added to the reaction mixture and the resulting mixture was extracted with methylene chloride, the methylene chloride layer was washed with water twice and dried on anhydrous magnesium sulfate. The solvent was concentrated under vacuum and isopropanol was added to the residue to give 2.28 g of crystalline 3-[2-[4-(2-methoxyphenyl)-1-piperazinyl]-ethyl]-2,4-(1H,3H)quinazolinedione having a melting point of 217°–218° C. (recrystallized from chloroform-ether).

Elemental analysis: Calculated for $C_{21}H_{24}N_4O_3$: C 66.30, H 6.36, N 14.73 (%). Found: C 66.00, H 6.31, N 14.60 (%).

(b) 1-(2-Methoxyphenyl)-4-[2-(2-aminobenzoyl)aminoethyl]piperazine (3.54 g) and urea (1.2 g) were dissolved in dimethylformamide (20 ml) and the resulting solution was heated at an external temperature of 140° to 180° C. for 5 to 8 hours. After completion of the reaction, water (200 ml) was added to the reaction mixture and the resulting crystal was filtered off. Upon recrystallization from dioxane, 3-[2-[4-(2-methoxyphenyl)-1-piperazinyl]ethyl]2,4-(1H,3H)-quinazolinedione (3.5 g) was obtained as needles. Its physicochemical data was the same as that of the product obtained in (a).

EXAMPLE 2

The following three compounds were prepared by repeating the procedure of Example 1-(a):

(a) 8-methyl-3-[2-[4-(2-methoxyphenyl)-1-piperazinyl]ethyl]-2,4-(1H,3H)quinazolinedione with m.p. 219° C. (recrystallized from chloroform-ether);

(b) 6-methyl-3-[2-[4-(2-methoxyphenyl)-1-piperazinyl]ethyl]-2,4-(1H,3H)quinazolinedione with m.p. 208° C. (recrystallized from chloroform-ether); and (c) 7-chloro-3-[2-[4-(2-methoxyphenyl)-1-piperazinyl]ethyl]-2,4-(1H,3H)quinazolinedione with m.p. 224° C. (with decomposition and recrystallized from methanol).

EXAMPLE 3

(a) The 3-[2-[4-(2-methoxyphenyl)-1-piperazinyl]ethyl]-2,4-(1H,3H)quinazolinedione obtained in Example 1 was dissolved in chloroform and when the solution was saturated with hydrogen chloride gas, crystalline dihydrochloride was formed. m.p. 265°–266° C. (decomposed).

(b) The dihydrochloride obtained in (a) above was dissolved in cold water and upon standing, crystalline monohydrochloride formed. m.p. 268°–269° C. (with decomposition and recrystallized from water).

Elemental analysis: Calculated for $C_{21}H_{24}N_4O_3 \cdot HCl(\frac{1}{2}H_2O)$: C 59.22, H 6.15, N 13.15 (%). Found: C 59.02, H 5.91, N 13.05 (%).

EXAMPLE 4

The 3-[2-[4-(2-methoxyphenyl)-1-piperazinyl]ethyl]-2,4-(1H,3H)quinazolinedione (7.61 g) obtained in Example 1 was suspended in chloroform methanol. After addition of maleic acid (2.32 g), the suspension was heated under reflux until the maleic acid was completely dissolved. After completion of the reaction, the solvent was concentrated under vacuum and methanol was added to the residue to produce a monomaleic acid salt of 3-[2-[4-(2-methoxyphenyl)-1-piperazinyl]ethyl]-2,4-(1H,3H)quinazolinedione with a melting point of 199° C. (with decomposition and recrystallized from methanol).

Elemental analysis: Calculated for $C_{21}H_{24}N_4O_3 \cdot C_4H_4O_4$: C 60.48, H 5.68, N 11.28 (%). Found: C 60.36, H 5.69, N 11.31 (%).

EXAMPLE 5

A mixture of 3-(2-chloroethyl)-2,4-(1H,3H)-quinazolinedione (1.57 kg), 1-(2-methoxyphenyl)piperazine (1.34 kg), sodium iodide (1.05 kg) and potassium carbonate (0.49 kg) was dissolved in dimethylformamide (7,000 ml) and the solution was heated at an internal temperature of 80°–85° C. for 7 hours. After completion of the reaction, the mixture was cooled by the addition of water (25 l) and ice (5 kg). The cooled mixture was left for 24 hours and the resulting crystal was collected, washed with water and dried with heat to give 3-[2-[4-(2-methoxyphenyl)-1-piperazinyl]ethyl]-2,4-(1H,3H)quinazolinedione (2.3 kg). Its physicochemical data was the same as that of the products obtained in Example 1.

EXAMPLE 6

To a suspension of 60% sodium hydride (0.44 g) in dimethylformamide (50 ml), was added 3-[2-[4-(2-methoxyphenyl)-1-piperazinyl]ethyl]-2,4-(1H,3H)quinazolinedione (3.80 g) in a small portion under a nitrogen stream, and the mixture was stirred at room temperature for 30 minutes and at 50° C. for 10 minutes. After cooling to room temperature, a solution of ethyl 7-bromoheptanoate (2.37 g) in dimethylformamide (20 ml) was added to the mixture and the resulting mixture was stirred at room temperature overnight. The solvent was distilled off under vacuum and the resulting residue was extracted with chloroform. The chloroform layer was washed with water and dried with sodium sulfate. When the solvent was distilled off under vacuum, an oily substance was obtained and upon column chromatography on silica gel (eluted with a chloroformethanol 25:1 mixture), a pale yellow oil of 1-(6-ethoxycarbonylhexyl)-3-[2-[4-(2-methoxyphenyl)-1-piperazinyl]ethyl]-2,4-(1H,3H)quinazolinedione (3.62 g) was obtained. The oil was dissolved in ethanol (50 ml) and hydrogen chloride gas was introduced into the solution for about 5 minutes. After distilling off the solvent, the crystalline residue was recrystallized from a mixture of ethanol and n-hexane to give colorless needles of 1-(6-ethoxycarbonylhexyl)-3-[2-[4-(2-methoxyphenyl)-1-piperazinyl]ethyl]-2,4-(1H,3H)quinazolinedione dihydrochloride (3.45 g) having a m.p. of 109°–111° C.

Elemental analysis: Calculated for $C_{30}H_{40}N_4O_5 \cdot 2HCl(\frac{1}{2}H_2O)$: C 58.25, H 7.01, N 9.06 (%). Found: C 58.48, H 6.91, N 9.09 (%).

EXAMPLE 7

The following compounds (a) to (k) were prepared by repeating the procedure of Example 6. Compounds (i) to (k) were obtained in their pure forms rather than in hydrochloride forms.

(a) 1-(5-ethoxycarbonylpentyl)-3-[2-[4-(2-methoxyphenyl)-1-piperazinyl]ethyl]-2,4-(1H,3H)quinazolinedione dihydrochloride with m.p. 101° C. (recrystallized from ethanol-ether).

Elemental analysis: Calculated for $C_{29}H_{38}N_4O_5 \cdot 2HCl$: C 58.48, H 6.77, N 9.41 (%). Found: C 58.76, H 6.80, N 9.97 (%).

(b) 1-(4-ethoxycarbonylbutyl)-3-[2-[4-(2-methoxyphenyl)-1-piperazinyl]ethyl]-2,4-(1H,3H)quinazolinedione dihydrochloride with m.p. 140° C. (recrystallized from ethanol-ether).

Elemental analysis: Calculated for $C_{28}H_{36}N_4O_5 \cdot 2HCl(\frac{1}{2}H_2O)$: C 56.95, H 6.66, N 9.49 (%). Found: C 57.12, H 6.53, N 9.48 (%).

(c) 1-(3-ethoxycarbonylpropyl)-3-[2-[4-(2-methoxyphenyl)-1-piperazinyl]ethyl]-2,4-(1H,3H)quinazolinedione dihydrochloride with m.p. 184° C. (with decomposition and recrystallized from ethanol-n-hexane).

Elemental analysis: Calculated for $C_{27}H_{34}N_4O_5 \cdot 2HCl(\frac{1}{2}H_2O)$: C 56.25, H 6.47, N 9.72 (%). Found: C 55.95, H 6.13, N 10.02 (%).

(d) 1-(6-methoxycarbonyl-2-hexynyl)-3-[2-[4-(2-methoxyphenyl)-1-piperazinyl]ethyl]-2,4-(1H,3H)quinazolinedione dihydrochloride with m.p. 128° C. (with decomposition: recrystallized from ethanol-n-hexane).

Elemental analysis: Calculated for $C_{29}H_{34}N_4O_5 \cdot 2HCl \cdot \frac{1}{2}H_2O$: C 58.00, H 6.21, N 9.33 (%). Found: C 57.81, H 5.91, N 9.23 (%).

(e) 1-heptyl-3-[2-[4-(2-methoxyphenyl)-1-piperazinyl]ethyl]-2,4-(1H,3H)quinazolinedione dihydrochloride with m.p. 114°–116° C. (recrystallized from ethanol-n-hexane).

Elemental analysis: Calculated for $C_{28}H_{38}N_4O_3 \cdot 2HCl$: C 60.97, H 7.31, N 10.16 (%). Found: C 61.36, H 7.31, N 10.68 (%).

(f) 1-pentyl-3-[2-[4-(2-methoxyphenyl)-1-piperazinyl]ethyl]-2,4-(1H,3H)quinazolinedione dihydrochloride with m.p. 148° C. (recrystallized from methanol-ether).

Elemental analysis: Calculated for $C_{26}H_{34}N_4O_3 \cdot 2HCl$: C 59.65, H 6.93, N 10.70 (%). Found: C 59.94, H 6.88, N 10.41 (%).

(g) 1-(3-butenyl)-3-[2-[4-(2-methoxyphenyl)-1-piperazinyl]ethyl]-2,4-(1H,3H)quinazolinedione dihydrochloride with m.p. 157° C. (recrystallized from methanol-ether).

Elemental analysis: Calculated for $C_{25}H_{30}N_4O_3 \cdot 2HCl(\frac{1}{2}H_2O)$: C 58.14, H 6.44, N 10.85 (%). Found: C 58.61, H 6.35, N 10.62 (%).

(h) 1-isopropyl-3-[2-[4-(2-methoxyphenyl)-1-piperazinyl]ethyl]-2,4-(1H,3H)quinazolinedione dihydrochloride with m.p. 178° C. (with decomposition: recrystallized from ethanol-n-hexane).

Elemental analysis: Calculated for $C_{24}H_{30}N_4O_3 \cdot 2HCl(\frac{1}{2}H_2O)$: C 57.14, H 6.59, N 11.11 (%). Found: C 57.10, H 6.35, N 10.92 (%).

(i) 1-methyl-3-[2-[4-(2-methoxyphenyl)1-piperazinyl]ethyl]-2,4-(1H,3H)quinazolinedione with m.p. 154°–155° C. (recrystallized from ethanol-ether).

Elemental analysis: Calculated for $C_{22}H_{26}N_4O_3$: C 66.99, H 6.64, N 14.20 (%). Found: C 66.91, H 6.66, N 14.17 (%).

(j) 1-(3-oxotrans-1-octenyl)3-[2-[4-(2-methoxyphenyl)-1-piperazinyl]ethyl]-2,4-(1H,3H)quinazolinedione (as an oil).

Elemental analysis: Calculated for $C_{29}H_{36}N_4O_4$: C 69.02, H 7.19, N 11.10 (%). Found: C 68.72, H 7.21, N 10.98 (%).

(k) 1-(5-oxohexyl)-3-[2-[4-(2-methoxyphenyl)-1-piperazinyl]ethyl]-2,4-(1H,3H)quinazolinedione (as an oil).

Elemental analysis: Calculated for $C_{27}H_{34}N_4O_4$: C 67.76, H 7.16, N 11.71 (%). Found: C 67.46, H 6.90, N 11.41 (%).

EXAMPLE 8

The 1-(3-ethoxycarbonylpropyl)3-[2-[4-(2-methoxyphenyl)-1-piperazinyl]ethyl]-2,4-(1H,3H)quinazolinedione (4.53 g) obtained in Example 7-c) was dissolved in ethanol (40 ml). After adding 2N aqueous sodium hydroxide under cooling with ice, the resulting mixture was stirred at room temperature for 3 hours. The solvent was distilled off under vacuum and the residue was dissolved in water (20 ml). When the pH of the solution was adjusted to 7 with 10% aqueous hydrochloric acid, a crystal formed. It was filtered off and recrystallized from a mixture of ethanol and n-hexane to provide pale yellow needles of 1-(3-carboxypropyl)-3-[2-[4-(2-methoxyphenyl)-1-piperazinyl]ethyl]-2,4-

(1H,3H)quinazolinedione (2.52 g) with a m.p. of 182° C. (decomposed).

Elemental analysis: Calculated for $C_{25}H_{30}N_4O_5$: C 64.36, H 6.48, N 12.01 (%). Found: C 64.11, H 6.48, N 11.87 (%).

EXAMPLE 9

The 1-(3-oxo-trans-1-octenyl)-3-[2-[4-(2-methoxyphenyl)-1-piperazinyl]ethyl]-2,4-(1H,3H)quinazolinedione (1.80 g) obtained in Example 7-(j) was dissolved in ethanol (20 ml). After addition of sodium borohydride (163 mg), the mixture was stirred at room temperature for 2 hours. Then, the pH of the mixture was adjusted to 7 with 10% aqueous hydrochloric acid and the solvent was distilled off under vacuum. The residue was extracted with chloroform, and the chloroform layer was washed with water and dried with sodium sulfate. When the solvent was distilled off under vacuum, an oily product (1.7 g) was obtained, and 500 mg of it was purified by silica gel preparative TLC (developed with a chloroform-ethanol 20:1 mixture). The resulting crystal was recrystallized from a mixture of benzene and n-hexane to give a colorless acicular crystal of 1-(3-hydroxy-trans-1-octenyl)-3-[2-[4-(2-methoxyphenyl)-1-piperazinyl]ethyl]-2,4-(1H,3H)quinazolinedione (350 mg) having a m.p. of 118°–119° C.

Elemental analysis: Calculated for $C_{29}H_{38}N_4O_4$: C 68.75, H 7.56, N 11.06 (%). Found: C 69.02, H 7.58, N 11.02 (%).

EXAMPLE 10

To a suspension of 60% sodium hydride (0.44 g) in dimethylformamide (50 ml), 3-[2-[4-(2-methoxyphenyl)-1-piperazinyl]ethyl]-2,4-(1H,3H)quinazolinedione (3.80 g) was added in a small portion under a nitrogen stream, and the mixture was stirred at room temperature for 30 minutes and at 80° C. for 10 minutes. After cooling to room temperature, a solution of 1-acetoxy-5-chloropropane (1.98 g) in dimethylformamide (10 ml) and sodium iodide (1.8 g) were added to the mixture, and the resulting mixture was held at 80° C. for 2 hours. After completion of the reaction, water (30 ml) was added and the solvent was distilled off under vacuum. The residue was extracted with chloroform, and the chloroform layer was washed with water and dried with sodium sulfate. By distilling off the solvent under vacuum, an oily substance was formed and this was purified by silica gel column chromatography (eluted with a chloroform-methanol 100:1 mixture) to provide a pale yellow oil of 1-(5-acetoxypentyl)-3-[2-[4-(2-methoxyphenyl)-1-piperazinyl]ethyl]-2,4-(1H,3H)quinazolinedione. This was dissolved in methanol (50 ml), and after addition of a great excess of aqueous sodium hydroxide, the mixture was stirred at room temperature for one hour. After completion of the reaction, the solvent was distilled off under vacuum, and the resulting residue was extracted with chloroform. The chloroform layer was washed with water and dried with sodium sulfate. By distilling off the solvent under vacuum, a pale yellow oil of 1-(5-hydroxypentyl)-3-[2-[4-(2-methoxyphenyl)-1-piperazinyl]ethyl]-2,4-(1H,3H)quinazolinedione was obtained. This was dissolved in methanol (ca. 50 ml) and hydrogen chloride gas was introduced into the solution for about 5 minutes. Then, the solvent was distilled off under vacuum and the resulting crystalline residue was recrystallized from a mixture of water, methanol and diethyl ether to provide needles of 1-(5-hydroxypentyl)-3-[2-[4-(2-methoxyphenyl)-1-piperazinyl]ethyl]-2,4-(1H,3H)quinazolinedione dihydrochloride (2.1 g) with a m.p. of 154°–156° C.

Elemental analysis: Calculated for $C_{26}H_{34}N_4O_4.2HCl(\frac{1}{2}H_2O)$: C 56.93, H 6.80, N 10.21 (%). Found: C 57.35, H 6.73, N 10.37 (%).

EXAMPLE 11

The following compounds was prepared by repeating the procedure of Example 10.

1-(2-hydroxyethyl)3-[2-[4-(2-methoxyphenyl)-1-piperazinyl]ethyl]-2,4-(1H,3H)quinazolinedione dihydrochloride with m.p. 210° C. (recrystallized from water-ethanol-ether).

Elemental analysis: Calculated for $C_{23}H_{28}N_4O_4.2HCl(\frac{1}{2}H_2O)$: C 54.55, H 6.17, N 11.06 (%). Found: C 54.43, H 6.17, N 10.79 (%).

EXAMPLE 12

A mixture of 7-chloro-6-sulfamoylisatoic anhydride (7.45 g) and 1-(2-aminoethyl)-4-(2-methoxyphenyl)piperazine (6.64 g) was dissolved in methanol (100 ml), and the resulting mixture was heated under reflux for 3 hours under a nitrogen stream. After completion of the reaction, the solvent was distilled off under vacuum and the residue was recrystallized from methanol-acetone and dried to give 2-amino-4-chloro-5-sulfamoyl-N-[2-[4-(2-methoxyphenyl)-1-piperazinyl]ethyl]benzamide.

A solution of this benzamide derivative (1.32 g) in acetic acid (20 ml) was added dropwise to a solution of phosgene (2.33 g) in toluene (10 ml) under stirring at room temperature. Then, the mixture was refluxed for one hour and cooled to room temperature. The resulting crystal was filtered and suspended in a mixture of methanol (10 ml) and water (10 ml), and after passing hydrogen chloride gas into the suspension for about 5 minutes, the solvent was distilled off under vacuum to provide a crystalline residue. It was recrystallized from water-methanol-ether to give colorless needles crystal of 7-chloro-6-sulfamoyl-3-[2-[4-(2-methoxyphenyl)-1-piperazinyl]ethyl]-2,4-(1H,3H)quinazolinedione hydrochloride (200 mg) having a m.p. of 266°–268° C. (with decomposition).

Elemental analysis: Calculated for $C_{21}H_{24}ClN_5O_5S.HCl.\frac{1}{2}H_2O$: C 46.76, H 4.86, N 12.98 (%). Found: C 46.47, H 4.86, N 12.22 (%).

What is claimed is:

1. A phenylpiperazine derivative of the formula:

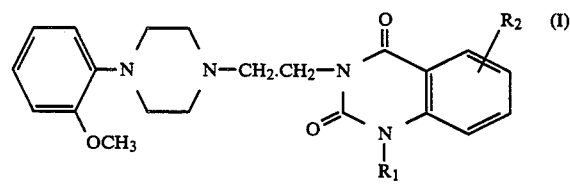

wherein $R_1$ is a hydrogen atom or a straight- or branched-chain saturated or unsaturated alkyl group having 1 to 8 carbon atoms which may be substituted at any position by a hydroxyl group, a carboxyl group, a lower alkoxycarbonyl group or an oxo group; and $R_2$ is a hydrogen atom, a halogen atom, a lower alkyl group or a sulfamoyl group.

2. A compound according to claim 1 which is represented by the formula:

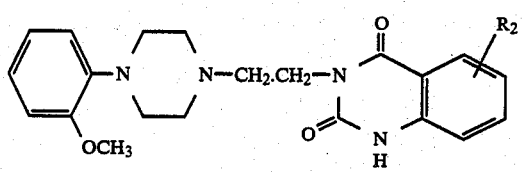

(wherein $R_2$ is a hydrogen atom, a halogen atom, a lower alkyl group or a sulfamoyl group).

3. A compound according to claim 2 which is represented by the formula:

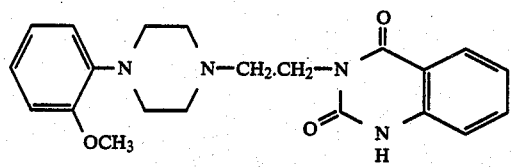

4. A compound of the formula:

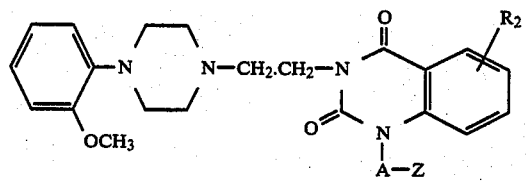

(wherein $R_2$ is a hydrogen atom, a halogen atom, a lower alkyl group or a sulfamoyl group; A is a straight- or branched-chain alkylene group having 1 to 7 carbon atoms; Z is a hydroxyl group, a carboxyl group or a lower alkoxycarbonyl group).

5. A compound according to claim 4 which is represented by the formula:

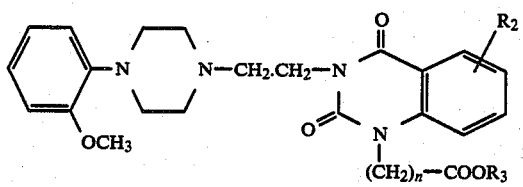

(wherein $R_2$ is a hydrogen atom, a halogen atom, a lower alkyl group or a sulfamoyl group; $R_3$ is a hydrogen atom or a lower alkyl group having 1 to 3 carbon atoms; and n is an integer of 1 to 7).

* * * * *